United States Patent [19]

Bresser et al.

[11] Patent Number: 5,521,061
[45] Date of Patent: May 28, 1996

[54] ENHANCEMENT OF PROBE SIGNAL IN NUCLEIC ACID-MEDIATED IN-SITU HYBRIDIZATION STUDIES

[75] Inventors: Joel Bresser, Bellaire; Michael L. Cubbage; Nagindra Prashad, both of Houston; William D. Weber, Bellaire; Shyh Chen Ju, Houston, all of Tex.

[73] Assignee: Aprogenex, Inc., Houston, Tex.

[21] Appl. No.: 916,068

[22] Filed: Jul. 17, 1992

[51] Int. Cl.$^6$ .............................. C12Q 1/68; C07H 21/04
[52] U.S. Cl. .................... 435/5; 435/6; 435/7.1; 435/7.2; 435/7.92; 435/810; 436/501; 436/63; 536/22.1; 536/23.7; 536/24.1; 935/78; 935/110
[58] Field of Search ................... 435/6, 7.1, 7.2, 435/7.92, 810, 5; 436/501, 63; 536/22.1–24.1; 935/78, 110

[56] References Cited

U.S. PATENT DOCUMENTS

| | | | |
|---|---|---|---|
| 4,034,073 | 7/1977 | Weetall | 424/1 |
| 4,121,975 | 10/1978 | Ullman et al. | 195/99 |
| 4,302,204 | 11/1981 | Wahl et al. | 23/230.3 |
| 4,423,153 | 12/1983 | Ranney et al. | 436/63 |
| 4,483,920 | 11/1984 | Gillespie et al. | 435/6 |
| 4,798,804 | 1/1989 | Khanna et al. | 436/94 |
| 4,886,741 | 12/1989 | Schwartz | 435/5 |
| 5,032,503 | 7/1991 | Khanna et al. | 435/7.6 |
| 5,037,745 | 8/1991 | McAllister | 435/91 |
| 5,077,210 | 12/1991 | Eigler et al. | 435/176 |
| 5,106,730 | 4/1992 | Van Ness et al. | 435/6 |
| 5,124,444 | 6/1992 | Van Ness et al. | 536/27 |
| 5,130,238 | 7/1992 | Malek et al. | 435/91 |
| 5,166,195 | 11/1992 | Ecker | 514/44 |
| 5,376,529 | 12/1994 | Van Ness et al. | 435/6 |

FOREIGN PATENT DOCUMENTS

| | | | |
|---|---|---|---|
| 238332 | 9/1987 | European Pat. Off. | C12Q 1/68 |
| WO90/02173 | 3/1990 | WIPO | C12N 7/100 |
| 9010715 | 9/1990 | WIPO | C12Q 1/68 |
| WO91/02088 | 2/1991 | WIPO | C12Q 1/68 |

OTHER PUBLICATIONS

Pajor et al. (1991) Histochemistry, vol. 96, pp. 73–81.
*Sigma Chemical Company Catalog* (1990) (Sigma Chemical Co., St. Louis, MO, USA), pp. 552 and 867.
Halldon et al. (1989) J. of Immunological Meth., vol. 124, pp. 103–109.
*The Merck Index* (Merck & Co. Inc., 1989), p. 7509.
Maniatis et al., Published 1982, by Cold Spring Harbor Laboratory, Cold Spring Harbor, (New York, USA), "Molecular Cloning," pp. 208, 387, and 448.
Bauman et al., Issued 1981, The Journal of Histochemistry and Cytochemistry, "Cytochemical Hybridization and Fluorochrome–labeled RNA.," vol. 29, pp. 227–237.
Lambert, Issued 1982, Agric. Biol. Chem., "Pretreatment of Cells of *Klebsiella pneumoniae* with 50% (v/v) Dimethylsulfoxide Yields Purified Deoxyribonucleic Acid of Low Polysaccharide Content," vol. 46, pp. 3079–3080.
Pfister, et al., Permeation Enhancers Compatible with Transdermal Drug Delivery Systems, Part I: Selection and Formulation Considerations, Pharmaceutical Technology, pp. 132–140 (Sep. 1990).
Pfister, et al., Permeation Enhancers Compatible with Transdermal Drug Delivery Systems, Part II: System Design Considerations, Pharmaceutical Technology, pp. 54–60, (Oct. 1990).
Lee, Permeation Enhancers for the Nasal Delivery of Protein and Peptide Therapeutics, Biopharm., pp. 22–25, (Nov./Dec. 1990).
Stratton, Cyclodextrins and Biological Macromolecules, Biopharm., pp. 44–51, (Nov./Dec., 1991).

*Primary Examiner*—W. Gary Jones
*Assistant Examiner*—Ardin H. Marschel
*Attorney, Agent, or Firm*—Elman & Fried

[57] ABSTRACT

Solutions useful for hybridizing cells and viruses with nucleic acid and antibody probes, their usefulness increased due to the presence of permeation enhancers and signal enhancers, including permeation enhancers; also the hybridization processes wherein the solutions are used.

57 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: N ( x i ) SEQUENCE DESCRIPTION: SEQ ID NO:1:

ATCAGAGTAG  TGGTATTTCA  CCGGC                    2 5

( 2 ) INFORMATION FOR SEQ ID NO: 2:

( i ) SEQUENCE CHARACTERISTICS:
        ( A ) LENGTH: 25 base pairs ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: N ( x i ) SEQUENCE DESCRIPTION: SEQ ID NO:2:

TACGCTCGAT CCAGCTATCA GCCGT                                           2 5

ENHANCEMENT OF PROBE SIGNAL IN NUCLEIC ACID-MEDIATED IN-SITU HYBRIDIZATION STUDIES

FIELD OF THE INVENTION

The invention is related to nucleic acid hybridization assays and immunoassays performed on cells and viruses.

BACKGROUND OF THE INVENTION

In situ hybridization assays and immunoassays, which can be targeted for the nucleic acids and antigens of pathogenic viruses and microorganisms, as well as for those of human cells, provide important diagnostic tools. The value of such assays increases, however, if one increases the amount of detectable signal generated by a given amount of target-bound probe molecules. An important limiting factor for signal intensity is the permeability of the targets to the probe molecules. In in situ assays done with target cells, the probe molecules must diffuse through the outer membrane of target cells and to locations in the cell where the target molecules reside. The ability of the probe molecules to permeate the cells in such a manner will affect the amount of signal generated.

Another potential means of increasing the signal is to have a signal enhancing compound present during the final measurement of signal in the assay.

The present inventions involve the discovery of compounds useful as permeation and signal enhancers in in situ hybridization assays and immunoassays.

BRIEF SUMMARY OF THE INVENTION

The inventions are in situ hybridization assays and immunosassays in which permeation enhancers and signal enhancers, are used. The enhancers are members of a variety of chemical classes and include DMSO, aliphatic alkanes, alkenes, alcohols, cyclodextrins, sugars, fatty acid esters, lactams, organic silanes, and combinations thereof.

The assay solutions used in the process are also inventions.

THE PRIOR ART

Dimethyl sulfoxide (DMSO) has been identified as a permeation enhancer for lymphocytes where the probe is a fluorochrome, such as mithramycin, unattached to a nucleic acid or other molecule. (U.S. Pat. No. 4,423,153).

Lactams have been reported to be useful reagents in nucleic acid hybridization reactions (PCT application of Van Ness et al, number WO 91/02088)

Volume exclusion agents, such as polyethylene glycol and dextran sulfate have been used to improve in situ hybridization rates (U.S. Pat. No. 4,886,741).

A large number of compounds have been identified as permeation enhancers, but not where permeation involved antibody or nucleic acid probes traversing cellular membranes. For example, components have been disclosed as skin permeation enhancers where the barrier to be permeated is the outermost layer of skin, which comprises multiple layers of dead keratinized cells and is imbibed with lipids. (W. R. Pfister and D. S. T.-Hsieh, *Pharmaceutical Technology*, p. 132 (September 1990) and p.54 (October 1990). Additionally, a number of compounds have been disclosed as enhancers where the barrier is the nasal mucous membrane (W. A. Lee, *Biopharm.*, p.22 (November/December 1990).

Compounds reported as skin permeation enhancers include DMSO, ethanol, cyclodextrins, lactams, and isopropyl palmitate. (Pfister and Hsieh, September 1990).

Polyvinylpyrrolidone ("PVP") has been used as a reagent in hybridization reactions by Wahl et al (U.S. Pat. No. 4,302,204), Gillespie et al (U.S. Pat. No. 4,483,920) and Goodson et al (European Patent Application EP 238332).

Cyclodextrins have been identified as signal enhancers (*Bio/Pharm*, November/December 1991, p. 44–51).

TRITON X-100™ (an alcohol derivative of polyoxyethylene ether), used in conjunction with the enhancers in the present inventions, has been disclosed in PCT patent applications WO 90/02173 and Wo 90/02204.

DETAILED DESCRIPTION

In one aspect, the invention is a permeation enhancer-modified process of detecting a target molecule in a biological entity (cell or virus) which process comprises the steps of:

(1) contacting the biological entity with an assay solution comprising a probe molecule so as to allow the probe molecule to bind to the target molecule, and (2) detecting the probe molecule after it has bound to the target molecule, said assay solution comprising the probe molecule and a compound selected from the group dimethyl sulfoxide ("DMSO"), an alcohol, an aliphatic alkane, an alkene, a cyclodextrin, a fatty acid ester, an amide or lactam, and an organic silane, said probe molecule either a nucleic acid probe or an antibody probe.

The fact that a compound of the group, if added to the assay solution, increases the signal ultimately observed strongly suggests such a compound is a permeation enhancer. On that basis, the above invention is labeled here as a "permeation enhancer-modified" process. That designation is useful for distinguishing such an invention from a "signal enhancer-modified process, described below, wherein the enhancing compound is added after the cells or viruses have been removed from the assay solution, especially when the enhancing compound is present during the fluorimetric measurement which is the final step in such an assay.

An "antibody probe" is a probe that comprises an antibody moiety.

In a preferred embodiment of the permeation enhancer-modified process, wherein the target molecule is a nucleic acid molecule, the assay solution comprises a nucleic acid probe and DMSO (2 to 20 percent) and one or more compounds selected from the group, an alcohol (2 to 20 percent), an aliphatic alkane (2 to 20 percent), an alkene (2 to 20 percent), a cyclodextrin (2 to 20 percent), a fatty acid ester (2 to 20 percent) of the formula $R_1(COO)R_2$, an amide or lactam (2 to 15 percent) of the formula $R_3(NH)(CO)R_4$, and an organic silane (2 to 20 percent) of the formula $(SiR_5R_6R_7)N(SiR_8R_9R_{10})$, $(SiR_5R_6R_7)$—$(SiR_8R_9R_{10})$, $(SiR_5R_6R_7)O(SiR_8R_9R_{10})$, or $(SiR_5R_6O)(SiR_7R_8O)(SiR_9R_{10}O)$ and the combined volumes of DMSO and the compounds selected from the group not being more than 30 percent of the assay solution (v/v).

In a combination aspect of the permeation enhancer-modified process, the assay solution comprises a nucleic acid probe and DMSO (2 to 20 percent) and one or more compounds selected from the group, an alcohol (2 to 20 percent), an aliphatic alkane (2 to 20 percent), an alkene (2 to 20 percent), a cyclodextrin (2 to 20 percent), a fatty acid ester (2 to 20 percent) of the formula $R_1(COO)R_2$, an amide or lactam (2 to 15 percent) of the formula $R_3(NH)(CO)R_4$, and an organic silane (2 to 20 percent) of the formula $(SiR_5R_6R_7)N(SiR_8R_9R_{10})$, $(SiR_5R_6R_7)$—$(SiR_8R_9R_{10})$, $(SiR_5R_6R_7)O(SiR_8R_9R_{10})$, or $(SiR_5R_6O)(SiR_7R_8O)(SiR_9R_{10}O)$, the combined volumes of DMSO and the compounds selected from the group not being more than 30 percent of the assay solution (v/v).

In another variation of the permeation enhancer-modified process, in addition to DMSO, an alkene or (preferably) an alkane, and at least one other compound are selected from the group. Preferred structures are those described above as preferred.

In a particular embodiment of the permeation enhancer-modified process, the assay solution contains about 10 percent Triton X-100(v/v) (Triton X-100 is an alcohol derived of polyoxyethylene ether).

In particular preferred embodiments of the permeation enhancer-modified process, the only compound selected from the group is DMSO and the volume of DMSO is between 2 and 20 percent of that of the assay solution (v/v); it is particularly preferred that the volume of DMSO is about 10 percent of that of the assay solution (v/v).

It is preferred that the concentration of a compound be kept low enough so that none of it precipitates out of solution and so that no other compound in the assay solution precipitates. Alkanes, especially squalane and those similar in structure to squalane or larger than squalane, and alcohols, especially oleyl alcohol and those similar in structure or larger than oleyl alcohol, may—depending on what other ingredients are present—partially precipitate out of the assay solution when added to concentrations of 10 percent or higher.

In another aspect, the invention is a signal enhancer-modified process of detecting a target molecule in a biological entity which process comprises the steps of:

(1) contacting the biological entity with an assay solution comprising a probe molecule so as to allow the probe molecule to bind to the target molecule, and (2) removing the biological entity from the assay solution, (3) adding a signal enhancing compound to the solution in which the biological entity is suspended, (4) detecting, as the signal, light quanta generated directly or indirectly by the target-bound probe molecule, said signal enhancing compound selected from the group, an alcohol, an aliphatic alkane, a sugar, a fatty acid ester, an amide or lactam, and an organic silane.

Light quanta emitted by a fluorescent moiety of the probe molecule is considered to be quanta generated directly by the target-bound probe molecule. Light quanta emitted as a result of cleavage of a chemical bond within a reporter group (e.g., isoluminol) in a chemiluminescent group is also considered to be a photon that is emitted directly by a reporter group. Light quanta emitted by a scintillation fluid as a result of a radiant energy being emitted by a radioactive reporter group is considered to be quanta generated indirectly by the reporter group.

It is preferred that the signal enhancer be added to the solution in which the biological entity is suspended while the signal detection is made (the "detection solution"); i.e., during step (4).

The fact that a compound of the group, if added to the detection solution, increases the signal ultimately observed strongly suggests such a compound is a signal enhancer.

In a preferred embodiment of the signal enhancer-modified process, the detection solution comprises one or more compounds selected from the group, an alcohol (2 to 20 percent), an aliphatic alkane (2 to 20 percent), an alkene (2 to 20 percent), a cyclodextrin (2 to 20 percent), a fatty acid ester (2 to 20 percent) of the formula $R_1(COO)R_2$, an amide or lactam (2 to 15 percent) of the formula $R_3(NH)(CO)R_4$, and an organic silane (2 to 20 percent) of the formula $R_5SiOSiR_6$, the combined volumes of DMSO and the compounds selected from the group not being more than 30 percent of the assay solution (v/v).

The notation $R_1(COO)R_2$ stands for compounds with the structural formula

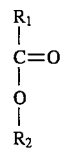

The notation $R_3(NH)(CO)R_4$ stands for compounds with the structural formula

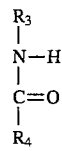

The notation $(SiR_5R_6R_7)N(SiR_8R_9R_{10})$ stands for compounds with the structural formula

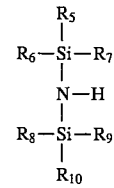

The notation $(SiR_5R_6R_7)$—$(SiR_8R_9R_{10})$ stands for compounds with the structural formula

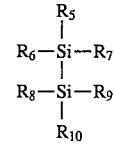

The notation $(SiR_5R_6R_7)O(SiR_8R_9R_{10})$ stands for compounds with the structural formula

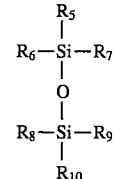

The notation $(SiR_5R_6O)(SiR_7R_8O)(SiR_9R_{10}O)$ stands for compounds with the structural formula

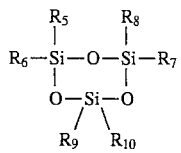

A solution that contains the enhancers specified for use in the process of this invention, or the combination of enhancers so specified, is also an invention.

Accordingly, for example, an additional invention here is a solution comprising a probe molecule and an enhancer selected from the group DMSO, an alcohol, an aliphatic alkane, a cyclodextrin, a fatty acid ester, an amide or lactam, and an organic silane. Furthermore, for example, another invention is a solution comprising a probe molecule and one or more compounds selected from the group, DMSO, an alcohol, an aliphatic alkane, a cyclodextrin, a fatty acid ester, an amide or lactam, and an organic silane, the volumes of compounds totalling not more than 20 percent of the solution (v/v).

A kit that contains, in addition to a probe molecule, the enhancers specified for use in the process of this invention, or the combination of enhancers so specified, is also an invention.

Accordingly, for example, an additional invention here is a kit comprising a probe molecule and an enhancer selected from the group DMSO, an alcohol, an aliphatic alkane, a cyclodextrin, a fatty acid ester, an amide or lactam, and an organic silane. Furthermore, for example, another invention is a kit comprising a probe molecule and a solution comprising one or more compounds selected from the group, DMSO, an alcohol, an aliphatic alkane, a cyclodextrin, a fatty acid ester, an amide or lactam, and an organic silane, the volumes of compounds totalling not more than 20 percent of the solution (v/v).

In the foregoing processes, solutions, and kits, $R_1$, $R_2$, $R_3$, $R_4$, $R_5$, $R_6$, $R_7$, $R_8$, $R_9$ and $R_{10}$ are alkyl carbon structures.

$R_1$ and $R_2$ may be covalently joined to form a ring structure.

$R_3$ and $R_4$ may be covalently joined to form a ring structure.

In the foregoing processes, a percent designated in parenthesis after a compound refers to the compound's concentration expressed as percent of the assay solution (v/v).

It is further preferred that the alcohol has between 2 and 40 carbon atoms; that aliphatic alkane has between 10 and 60 carbon atoms; that the alkene has between 10 and 60 carbon atoms, that $R_1$ plus $R_2$ together have between 3 and 20 carbon atoms and, where $R_1$ and $R_2$ are not covalently joined so as to form a ring, $R_1$ and $R_2$ each have at least one carbon atom; that $R_3$ plus $R_4$ together have between 2 and 20 carbon atoms and, where $R_3$ and $R_4$ are not covalently joined so as to form a ring, $R_3$ and $R_4$ each have at least one carbon atom; and that $R_5$, $R_6$, $R_7$, $R_8$, $R_9$ and $R_{10}$, each have at least one carbon atom, that the six alkyl carbon structures, $R_5$, $R_6$, $R_7$, $R_8$, $R_9$ and $R_{10}$, together have no more than 20 carbon atoms.

In process embodiments even more preferred: the alcohol has between 3 and 30 carbon atoms, the aliphatic alkane has between 20 and 40 carbon atoms, $R_1$ plus $R_2$ together have between 3 and 10 carbon atoms and, where $R_1$ and $R_2$ are not covalently joined so as to form a ring, $R_1$ and $R_2$ each have at least 3 carbon atoms;

$R_3$ plus $R_4$ together have between 3 and 10 carbon atoms and, where $R_3$ and $R_4$ are not covalently joined so as to form a ring, $R_3$ and $R_4$ each have at least 1 carbon atom; and $R_5$, $R_6$, $R_7$, $R_8$, $R_9$ and $R_{10}$, each have at least one carbon atom, that the six alkyl carbon structures,$R_5$, $R_6$, $R_7$, $R_8$, $R_9$ and $R_{10}$, together have no more than 10 carbon atoms.

Preferred alkenes for use as permeation enhancers are those where the ratio of carbon—carbon double bonds to carbon—carbon single bonds is less than one to three. Most preferably the ratio is less than one in ten.

The target cell or virus may be suspended in solution and not immobilized on a solid support. Alternatively, the target cell or virus is immobilized on a solid support.

The target cells may be substantially separated single cells as opposed to tissue sections. Alternatively, the target cells (or viruses) may be part of a tissue section (histologic section).

The cells containing a target molecule may be eukaryotic cells (e.g. human cells), prokaryotic cells (e.g., bacteria), plant cells, or any other type of cell. They can be simple eukaryotes such as yeast or be derived from more complex eukaryotes such as humans.

The target molecules can be in a non-enveloped virus or an enveloped virus (having an enveloping membrane such as a lipid-protein membrane).

The target nucleic acid molecules may be DNA molecules, RNA molecules or both DNA and RNA molecules.

The probes may be detectably labeled prior to addition to the hybridization solution. Alternatively, a detectable label may be selected which binds to the reaction product. Probes may be labeled with any detectable group for use in practicing the invention. Such detectable group can be any material having a detectable physical or chemical property. Such detectable labels have been well-developed in the field of immunoassays and in general most any label useful in such methods can be applied to the present invention. Particularly useful are enzymatically active groups, such as enzymes (see *Clin. Chem.*, 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see *Clin. Chem.*, 25:353 (1979)); chromophores; luminescers such as chemiluminescers and bioluminescers (see *Clin. Chem.*, 25:512 (1979)); specifically bindable ligands; proximal interacting pairs; and radioisotopes such as $^3H$, $^{35}S$, $^{32}P$, $^{125}I$ and $^{14}C$.

Nucleic acid probes can be used against a variety of viral and cellular nucleic acid target molecules. The target may be a DNA target such as a gene (e.g., oncogene), control element (e.g., promoter, repressor, or enhancer), or sequence coding for ribosomal RNA, transfer RNA, or RNase P. The target may be RNA such as mRNA, ribosomal RNA, RNase P, tRNA, a viral genome or complementary copy thereof. Additionally, the target may be a "nucleic acid amplification product," i.e., a nucleic acid molecule, either DNA or RNA, which is the result of introducing an enzyme or enzymes into the cell so that such enzymes will make an nucleic acid molecule complementary to one already present in the cell. For example, O. Bagasra et al, *The New England Journal of Medicine*, 326, pp. 1385–1391 (1992), have disclosed the use of the polymerase chain reaction (PCR) with intact cells such that the introduction of polymerase molecules into a cell resulted in additional nucleic acid molecules being formed, each a copy of one previously existing in the cell, though not necessarily existing before the introduction of the enzymes.

A viral nucleic acid target can be part of a virus (e.g., human immunodeficiency virus), in which case the virus may or may not be part of a cell. Alternatively, a viral nucleic acid target may not be part of a virus, but may be inside a cell.

The processes will result in enhancement when either antibody or oligonucleotide probes normally used in in situ hybridization are used. It will lead to enhancement when the probes are linked to fluorescent dyes or other detectable labels that normally allow the probes to hybridize to their target. Preferred oligonucleotides are those between about 15 and 1500 nucleotides in size; for targets in the cell nucleus, probes less than 40 nucleotides in length are preferred. The fluorescent dye molecule linked to the oligonucleotide may be fluorescein isothiocyanate (FITC), Texas Red, or any other fluorescent dye. More than one dye molecule may be added to the oligonucleotide. Processes for linking dye molecules to oligonucleotides have, for example been published for FITC by Agrawal and Zamecnik, *Nucleic Acid Res.* 18, 5419 (1990).

In a particular embodiment of the permeation enhancer-modified process, the assay solution further comprises an alcohol derivative of polyoxyethylene ether (Triton X- 100, see Aldrich Chemical Co. catalogue for 1990–91).

The amount of Triton in the assay solution will preferably be about 10% The cells can come from solid tissue (e.g., nerves, muscle, heart, skin, lungs, kidneys, pancreas, spleen, lymph nodes, testes, cervix, and brain) or cells present in membranes lining various tracts, conduits and cavities (such as the gastrointestinal tract, urinary tract, vas deferens, uterine cavity, uterine tube, vagina, respiratory tract, nasal cavity, oral cavity, pharynx, larynx, trachea, bronchi and lungs) or cells in an organism's fluids (e.g., urine, stomach fluid, sputum, blood and lymph fluid) or stool.

Preferably cells containing a target molecule will have been either treated with a fixative prior to their incubation with the assay solution or the assay solution will itself include a fixative. Fixatives are compounds that kill a cell but preserve its morphology and/or nucleic acids for an extended period of time. They act either by creating covalent linkages between cellular molecules or by precipitating certain intracellular molecules. Cross-linking fixatives include formaldehyde, glutaraldehyde, paraformaldehyde, ethyldimethyl-aminopropyl-carbodiimide, and dimethylsilserimidate. Precipitants include ethanol, acetic acid, methanol, acetone, and combinations thereof. It is further preferred that glacial acetic acid be included as a fixative when the cells are to be monitored by flow cytometry. If a cross-linking fixative is used, paraformaldehyde (0.1% v/v to 4% v/v is preferred, 0.5% v/v to 1% v/v is especially preferred; 2 hours to 20 hours preferred). Formaldehyde and gluteraldehyde are among the other possibilities. Fixatives are used at concentrations which do not destroy the ability of the cell's nucleic acids to hybridize to the probe. Other useful fixatives will be obvious to one skilled in the art. Fixatives and hybridization of fixed cells, in general, are discussed in PCT international applications, WO 90/02173 and WO 90/02204 of Research Development Corp.

Cross-linking agents, while preserving ultrastructure, often reduce hybridization efficiency; they form networks trapping nucleic acids and antigens and rendering them inaccessible to probes and antibodies. Some also covalently modify nucleic acids preventing later hybrid formation.

The assay solution may typically comprise a chaotropic denaturing agent, a buffer, a pore forming agent, a hybrid stabilizing agent.

The chaotropic denaturing agents (Robinson, D. W. and Grant, M. E. (1966) J. Biol. Chem. 241: 4030; Hamaguchi, K. and Geiduscheck, E. P. (1962) J. Am. Chem. Soc. 84: 1329) include formamide, urea, thiocyanate, guanidine, trichloroacetate, tetramethylamine, perchlorate, and sodium iodide. Any buffer which maintains pH at least between 7.0 and 8.0 may be utilized.

The pore forming agent is for instance, a detergent such as Brij 35, Brij 58, sodium dodecyl sulfate, CHAPS™ TRITON X-100™. Depending on the location of the target biopolymer, the pore-forming agent is chosen to facilitate probe entry through plasma, or nuclear membranes or cellular compartmental structures. For instance, 0.05% Brij 35 or 0.1% TRITON X-100™ will permit probe entry through the plasma membrane but not the nuclear membrane. Alternatively, sodium desoxycholate will allow probes to traverse the nuclear membrane. Thus, in order to restrict hybridization to the cytoplasmic biopolymer targets, nuclear membrane pore-forming agents are avoided. Such selective subcellular localization contributes to the specificity and sensitivity of the assay by eliminating probe hybridization to complementary nuclear sequences when the target biopolymer is located in the cytoplasm. Agents other than detergents such as fixatives may serve this function. Some of the enhancers that are used in the present inventions may function as pore-forming agents.

Hybrid stabilizing agents such as salts of mono- and di-valent cations are included in the hybridization solution to promote formation of hydrogen bonds between complementary sequences of the probe and its target biopolymer. Preferably sodium chloride at a concentration from 0.15M to 1M is used. In order to prevent non-specific binding of nucleic acid probes, nucleic acids unrelated to the target biopolymers are added to the hybridization solution.

Many types of solid supports may be utilized to practice the invention. Supports which may be utilized include, but are not limited to, microporous beads or sponges, glass, Scotch tape (3M), nylon, Gene Screen Plus (New England Nuclear), magnetic particles and nitrocellulose. Most preferably glass microscope slides are used. The use of these supports and the procedures for depositing specimens thereon will be obvious to those of skill in the art. The choice of support material will depend upon need for the procedure used to for visualize or analyze cells and the quantitation procedure used. Some filter materials are not uniformly thick and, thus, shrinking and swelling during in situ hybridization procedures is not uniform. In addition, some supports which autofluoresce will interfere with the determination of low level fluorescence. Glass microscope slides are most preferable as a solid support since they have high signal-to-noise ratios and can be treated to better retain tissue.

Reagents can be purchased from any of a variety of sources including Aldrich Chemical Co., Milwaukee, Wis., Sigma Chemical Co., St. Louis, Mo., Molecular Probes, Inc., Eugene, Oreg., Clontech, Palo Alto, Calif., Kodak, Rochester, N.Y., and SPectrum Chemical Manufacturing Corp., Gardenea, Calif.

Flow Cytometry

A Coulter Profile II flow cytometer was used for flow cytometry. With FITC as the probe dye, the filter for LFL3 was a 635 nm long pass filter and the filter for LFL1 was a 540 bp filter; the excitation wavelength was 488 nm. PMT1 and PMT3 settings were adjusted as required. A typical useful setting when fluorescein is the dye moiety is to have a PMT1 setting of 1100, a PMT3 setting of 900, and color compensation (PMT1, PMT3) of 15 percent.

Solutions Used for Experiments Described in Examples

A hybridization cocktail "HC" is a solution with the following composition: 5X SSC, 15X Ficoll/PVP, 0.16M sodium phosphate buffer (pH6), 1 mg/ml sheared salmon sperm DNA, 10% TRITON X-100™, 0.4M guanidinium isothiocyanate, 30% (v/v) formamide, 10 mM ethylene diamine tetraacetic acid ("EDTA"), 1.5% polyethylene glycol ("PEG"), 25 mM DTT (dithiothreitol), and 5 to 10 ug/ml (microgram/ml) probe.

A hybridization cocktail "HC-DMSO" is a solution with the following composition: 5X SSC, 15X Ficoll/PVP, 0.16M sodium phosphate buffer (pH6), 1 mg/ml sheared salmon sperm DNA, 10% TRITON X-100™, 0.4M guanidinium isothiocyanate, 30% (v/v) formamide, 10 mM ethylene aliamine tetraacetic acid ("EDTA"), 1.5% polyethylene glycol ("PEG"), 25 mM DTT (dithiothreitol), 10% (v/v) DMSO, and 5 to 10 ug/ml probe. In the foregoing, 500X Ficoll/PVP is 5 g of Ficoll type 400 (polysucrose, 400,000 mol wt) plus 5 g of PVP (polyvinylpyrrolidone) diluted to a total volume of 100 ml with water; 15X Ficoll/PVP is 500X Ficoll/PVP diluted with water by a factor of 15/500.

SSC was 0.15M sodium chloride, 0.015M sodium citrate, pH 7.0

0.1×SSC was SSC diluted 1:10 with water.

10×SSC was prepared so that, upon a 1:10 dilution with water, one obtains 1×SSC.

Fixation solution F, used in flow cytometry, had the following ingredients: 4 volumes ("vol") of ethanol plus 5 vol of 1×PBS solution plus 1 vol of glacial acetic acid.

Wash solution #1 had the following composition: 0.4M guanidinium isothiocyanate, 0.1% TRITON X-100™, 0.1 X SSC, in deionized water.

Wash solution #2 had the following composition: 0.1% TRITON X-100™, 0.1% SSC, in deionized water.

For fluorimetric measurements in the flow cytometer, cells were suspended in 1×PBS solution.

1×PBS was phosphate-buffered saline and had the formula, 0.136M NaCl, 0.003 M KCl, 0.008M $Na_2HPO_4 \cdot 7H_2O$, 0.001M $KH_2PO_4$.

Probes Used in Examples

The Y probe (also referred to as the HYR probe) was a collection of oligonucleotides specific for human Y chromosome α-satellite DNA repeated sequences; where the probe was to be detected under a fluorescent microscope, it was labeled at its 5' end, via an Aminolink linker molecule (aminohexyl, from Applied Biosystems, Inc.), to a Texas Red Moiety.

The 28S RNA probe was specific for ribosomal RNA and had the sequence:

ATCAGAGTAGTGGTATTTCACCGGC (SEQ ID NO: 1)

(In all sequences described herein, the 5' end is at the left end.)

The NR probe was specific for the nitrogen reductase gene found in bacteria and not eukaryotic cells. It had the sequence:

TACGCTCGATCCAGCTATCAGCCGT (SEQ ID NO: 2)

Cells Used in Examples

Hepg2 cells were a human cell line (American Type Culture Collection number, ATCC-HB8065).

WBC cells (white blood cells) were obtained from a healthy male human.

Amniotic cells were obtained by standard amniocentesis procedure.

Slide in situ Cell Preparation and Hybridization Protocol

1) Cells were suspended in a fixative (3 vol ethanol plus 1 vol methanol) and transferred to glass slides by centrifugation using a Cytospin apparatus.

2) The assay solution (consisting of the hybridization cocktail HC alone or mixed with a compound or compounds being tested as an enhancer) with the DNA probe (25 ul) was placed over the cells and covered with a coverslip.

3) The slide was heated at 90° C. for 5 minutes for DNA denaturation, then incubated at 46° C. for 30 minutes for hybridization.

4) Cells were washed once with the wash solution #1, which was equilibrated at 42° C. Then cells were washed ten times with wash solution #2, which was equilibrated at 42° C.

5) Mounting solution (50% glycerol (v/v) in 1×PBS plus the nuclear stain Hoechst, (#33258; 1 ug/ml) was placed on the cells and covered with a coverslip.

6) The hybridization signal was observed under an Olympus BH10 microscope with fluorescent capabilities using a rhodamine derivative filters (excitation wavelength of 567 nm, emission wavelength of 584 nm).

Liquid in Situ Cell Preparation and Hybridization Protocol

1. Cells were fixed in solution F, then resuspended in 2x SSC.

2. The cells were spun out of solution and resuspended in an assay solution (consisting of the hybridization cocktail HC alone or in combination with a compound or compounds being tested as an enhancer.)

3. After 30 min. at 42° C., the cells were washed in wash solution #1 preheated to 42° C. by centrifuging them out of the assay solution.

4. Cells were next washed in wash solution #2 preheated to 42° C.

5. Cells were resuspended in a 1X PBS solution containing 0.002% trypan blue as a counterstain.

6. Cells were run on a flow cytometer and a "Count vs. LFL1" histogram was generated. ("Count" refers to cell count.) This histogram was used as the basis for determining the mean LFL1.

Additional Useful Reagents and Solutions

Useful reagents and solutions for executing the inventions described herein include 0.0025% Evans Blue in the solution analyzed cytofluorimetrically; 5% (v/v) Vitamin E in the hybridization cocktail used where the assay target is in a biological entity; 5 μl of 1M (1 molar) DTT and 5 μl of Proteinase K (1 mg/ml) solution are added to 100 μl of cocktail and the hybridization reaction is run, for example, at 42° C. for 5 min, then at 95° C. for 5 min, and then at 42° C. for 2 min, when the target is in a biological entity; and/or about 0.05% or 0.10% aurintricarboxylic acid in the hybridization cocktail when the target is a biological entity and a fluorescent probe, especially one with a fluorescein or rhodamine derivative as a reporter group, is used.

Probes, where the target is in a biological entity can be made as phosphorothioate oligonucleotides, each 30-mer having four sulfur atoms, using an Applied Biosystem (ABI) DNA Synthesizer, Model 380B and the recommended ABI reagents. The sulfur atoms may be located as follows: one is at the extreme 5' end of the probe, a second is between the 7th and 8th nucleosides (counting from the 5' end), the third is between the 22nd and 23rd nucleosides, and the fourth is between the 29th and 30th nucleosides. The sulfur atoms of the polysulfurized oligonucleotides can then coupled to a fluorescent dye, iodoacetamido-fluorescein, as follows (smaller amounts can be synthesized by adjusting the volumes): 200 μg of dried oligonucleotide is dissolved in 100 μl of 250 mM Tris buffer, pH 7.4 to form a first solution. Then one mg of iodoacetamido-fluorescein is combined with 100 μl of dry dimethylformamide (i.e., 100 percent DMF) in a second solution. The two solutions are mixed together and shaken overnight. After the overnight incubation, the labeled oligonucleotide is precipitated with ethanol and 3M sodium acetate. This crude material is then loaded on to a PD-10 column to remove free dye. The desired fractions are then collected. The liquid phase is then removed under vacuum. The crude material is then purified with HPLC (high performance liquid chromatography).

Where 30-mers are used, probes against both strands of a double-stranded target can be used, provided that the probes are "out-of phase" along the map of the target so that any probe is not complementary in base sequence to more than about 15 nucleotides of a probe to the other strand of the target. In that way, probes hybridize to the target and not to each other.

EXAMPLES

In all Tables, all concentrations denoted as a "%" or a "percent" are v/v.

EXAMPLE 1

Effect of DMSO on Slide In Situ Hybridization

In this Example, the slide in situ cell preparation and hybridization protocol was followed. The results are shown in Table 1.

TABLE 1

| Cells | Assay Probe | Solution | Fluorescent Signal intensity (Scale of 1 to 4) |
|---|---|---|---|
| Hepg2 | Y-Probe | HC + 1.5% PEG | 4 |
| Hepg2 | Y-Probe | HC + 10% DMSO | 4 |
| WBC | Y-Probe | HC + 10% DMSO | 4 |
| Amniotic (male) | Y-Probe | HC + 10% DMSO | 4 |
| Amniotic (female) | Y-Probe | HC + 10% DMSO | 0 |

In Table 1, because HC contains 1.5% PEG, the final concentration of PEG in the test listed on the first line of the table was 3%.

The female cells used to generate the data in the last line of Table 1 constituted a negative control.

It was also observed that the combination of 10% Triton (non-ionic detergent) and 10% DMSO (sulfoxide) served as a better signal enhancer than these agents alone.

EXAMPLE 2

Effect of Various Compounds on In Situ Hybridization Signal

The inclusion of DMSO in an in situ assay solution increased the permeation of the nucleic acid probes into the cells and gave hybridization signal in over 95% of the cells. In this Example, we show the effect of adding, in addition to DMSO, 10 percent (v/v) of an additional compound to the assay solution. The additional compounds added were: squalane (an aliphatic alkane), dodecyl alcohol (an alcohol), beta-cyclodextrin (a sugar), isopropyl palmitate (a fatty acid ester), 1,2, propanediol (an alcohol), pyrrolidinone (a lactam) and hexamethyldisiloxane (an organic silane).

In this Example, the hybridization cocktail consisted of nine volumes of HC-DMSO plus one volume of an additional compound. In the control sample, one volume of water was added instead of one volume of additional compound. As a result, in all samples, the concentration of DMSO in the cocktail was 9 percent (v/v).

The Slide In Situ Cell Preparation and Hybridization protocol was followed. The cells used were Hepg 2 cells. The probe used was an HYR probe specific for human Y chromosome α-satellite DNA repeated sequences; at its 5' end, via an Aminolink linker molecule, the probe was linked to a Texas Red moiety. A signal intensity of 4 was assigned to the slide in which the assay solution was HC plus 10% DMSO (control slide) and all other slides were rated 1, 2, 3 or 4 in comparison to the control slide, depending on whether the intensity was 1, 2, 3, or 4 times that of the control slide, respectively.

The slide rating was then multiplied by 0.5 and listed in Table 2.

TABLE 2

| Additional compound in Hybridizaton cocktail | Fluorescent signal (Scale of 1 to 4) |
|---|---|
| water | 2 |
| dodecyl alcohol | 2 |
| squalane | 2 |
| oleic acid | 2 |
| beta-cyclodextrin | 1.5 |
| isopropyl palmitate | 1.5 |
| oleyl alcohol | 1.5 |
| 1,2-propanediol | 2 |
| hexamethyldisiloxane | 1 |
| 2-pyrrolidinone | 2 |

The results are an average of four independent experiments.

The results in Table 2 show that none of the additional compounds in combination with 9% DMSO increased DNA probe signal and brightness above that seen with 9% DMSO alone.

EXAMPLE 3

Effect of a Combination of Compounds on the Enhancement of DNA Signal in In Situ Hybridization This Example showed the effect of adding both squalane and an additional compound.

The Slide In Situ Cell Preparation and hybridization protocol was followed. The cells, probe, and probe concentration, was the same as in Example 2.

The hybridization cocktail consisted of 8 volumes of HC-DMSO, one volume of squalane, and one volume of additional compound. In the control sample, one volume of water was used instead of one volume of additional compound. As a result, in all samples, the concentrations of DMSO and squalane were 8 percent and 10 percent (v/v), respectively.

A signal intensity of 2 was assigned to the slide observed for the control sample. All other slides were rated 1,2,3 or 4 in comparison to the control sample slide, depending on whether the intensity was 0.5, 1.0, 1.5, or 2 times that of the control sample slide, respectively.

TABLE 3

| Additional compound in Hybridization cocktail | Signal Intensity (Scale of 1 to 4) |
| --- | --- |
| water | 2 |
| dodecyl alcohol | 4 |
| beta-cyclodextrin | 4 |
| isopropyl palmitate | 4 |
| 1,2-propanediol | 4 |
| pyrrolidinone | 4 |
| hexamethyldisiloxane | 4 |
| oleyl alcohol | 3 |
| triethanolamine | 1 |
| 10% triethanolamine - HCl | 2 |

In Table 3, the results are an average of four independent experiments.

The results in Table 3 show that, in many cases, the combination of squalane and an additional compound increased the signal brightness compared to 10% squalane alone in the in situ slide hybridization. DMSO, squalane and these additional compounds act as permeation enhancers in the experiments disclosed in the present application. Therefore the results in Table 3 indicate that, as regards the signal intensity observed, there is either a synergistic or unexpectedly additive effect of adding the additional permeation enhancer in addition to DMSO and squalane.

EXAMPLE 4

Effect of individual Permeation Enhancers on RNA Probe Signal in In Situ Liquid Hybridization The effect on probe signal intensity of adding, in addition to DMSO, additional compounds to the assay solution was determined in an in situ liquid hybridization assay. The data was analyzed by flow cytometry.

The Liquid In Situ Cell Preparation and Hybridization Protocol was followed. The cells used were Hela cells. The probes used were a 28S RNA probe (SEQ ID NO: 1) and an NR probe. Each probe (SEQ ID NO: 2) had an FITC moiety linked to its 5' end by an Aminolink crosslinker molecule (aminohexyl; purchased from Applied Biosystems, Inc.).

The 28S RNA probe (SEQ ID NO: 1) is a target-specific probe specific for ribosomal RNA fluorescence obtained with it represents the sum of fluorescence from target-bound probe, non-specifically bound probe and autofluorescence from cellular molecules. The NR probe (SEQ ID NO: 2) is specific for a plant nucleic acid sequence and, in the current Example, the fluorescence obtained with it represent the sum of fluorescence from non-specifically bound probe and autofluorescence.

In this experiment, the hybridization cocktail consisted of nine volumes of HC-DMSO plus one volume of additional compound. In the control sample, one volume of water replaced the one volume of additional compound. As a result, in all samples, the concentration of DMSO was 9 percent (v/v).

TABLE 4

| Additional compound in Hybridization cocktail | 28S RNA Probe | NR Probe | Ratio 28S RNA/NR |
| --- | --- | --- | --- |
| water | 6.070 | 0.137 | 44 |
| 10% pyrrolidinone | 10.19 | 0.133 | 77 |
| 10% B cyclodextrin | 9.593 | 0.135 | 71 |
| 10% hexamethyldisiloxane | 7.426 | 0.126 | 59 |
| 10% isopropyl palmitate | 8.057 | 0.140 | 58 |
| 10% propanediol | 8.227 | 0.148 | 56 |
| 10% dodecyl alcohol | 4.804 | 0.142 | 34 |
| 10% oleic acid | 3.643 | 0.142 | 26 |
| 10% oleyl alcohol | 0.731 | 0.136 | — |
| 10% squalane | 0.611 | 0.123 | — |

The ratio, 28S/NR, is the ratio of the mean LFL1 observed with the 28S RNA probe (SEQ ID NO: 1) to the mean LFL1 observed with the NR probe (SEQ ID NO: 2). The results in the "28S RNA probe" and "NR probe" columns give the mean LFL1 observed with the 28S RNA and NR probes, respectively (SEQ ID NO: 1 and SEQ ID NO: 2, respectively).

These results are from an average of four independent experiments. The results in Table 4 show that pyrrolidinone, β-cyclodextrin, hexamethyldisiloxane, isopropyl palmitate and propanediol, in combination with nine percent DMSO, increased the signal brightness compared to those obtained with nine percent DMSO alone. Nine percent is at or close to the optimal DMSO concentration for signal brightness if DMSO alone is used.

The use of either 10 percent squalane or 10 percent oleyl alcohol, lead to their precipitation from solution and resulting biphasic mixture in both cases. As a result, in both cases the signal intensity was markedly decreased.

EXAMPLE 5

The Effect of Permeation Enhancers on DNA Probe Signal in an In Situ Liquid Hybridization Assay The Liquid In Situ Cell Preparation and Hybridization Protocol was followed.

The "α-satellite" DNA probe is a target specific probe specific α-satellite DNA. Fluorescence obtained with it represents the sum of fluorescence from target-bound probe, non-specifically bound probe and autofluorescence from cellular molecules.

The effect of a combination of DMSO and squalane on the probe signal was measured as was that combination further enhanced with a third compound. The results are shown in Table 5.

The α-satellite DNA probe (SEQ ID NO: 2) and the NR probe all each had an FITC moiety linked to its 5' end by an Aminolink moiety.

In this Example, in all but two cases, the hybridization cocktail consisted of 9 volumes of HC-DMSO, a half volume of squalane, and a half volume of an additional compound. In one case, the additional compound was replaced by water, so that the hybridization compound consisted of 9 volumes of HC-DMSO, a half volume of squalane, and a half volume of water. In the control sample, the cocktail consisted of nine volumes of HC-DMSO and one volume of water. As a result, in all samples, there was 9 percent DMSO (v/v). When present, squalane was present at 5 percent. When present, the additional compound was present at 5%.

TABLE 5

| Squalane present? | Additional compound in cocktail | α-SAT Probe | NR Probe | Ratio α-SAT/NR |
|---|---|---|---|---|
| no | water | 3.829 | 0.175 | 22 |
| yes | water | 4.604 | 0.125 | 37 |
| yes | pyrrolidinone | 10.38 | 0.135 | 77 |
| yes | isopropyl palmitate | 5.988 | 0.117 | 52 |
| yes | 1,2 propanedial | 5.876 | 0.151 | 39 |
| yes | beta-cyclodextrin | 3.720 | 0.131 | 29 |

The ratio, α-SAT/NR, is the ratio of the mean LFL1 for the α-satellite DNA probe (SEQ ID NO: 2) to the mean LFL1 for the NR probe.

The results in Table 5 show that the assay solution with squalane plus DMSO increased the DNA probe signal intensity by 1.68-fold compared to the assay solution with DMSO alone. However, the combination of DMSO plus squalane plus either pyrrolidinone, isopropyl palmitate or 1,2, propanedial increased the DNA probe signal intensity by either 3.5, 2.4, or 1,8-fold, respectively, compared to 9% DMSO alone, thereby indicating an advantage to such combinations as opposed to the combination of DMSO and squalane alone.

EXAMPLE 6

Effect of Signal Enhancers on the Signal Intensity When Included in the Mounting Solution In this Example, the effectiveness of various compounds as signal enhancers was demonstrated by including them in the mounting solution but not solutions that the cell were suspended in prior to being suspended in the mounting solution.

After the in situ hybridization step, the cells were washed and then modified mounting solution was added and cells were observed under the microscope for fluorescence signal. Modified mounting solution was 9 volumes of mounting solution and one volume of additional compound, which was the compound being tested for its ability to be a signal enhancer. Mounting solution consisted of 0.1% 1,4 diphenylamine (antifade) in 50% glycerol (v/v), and nuclear stain Hoechst (#33258; 1 ug/ml).

Human female white blood cells (karyotype XX) were hybridized at 85° C. for 15 minutes with female chromosome HXR probes labelled with a rhodamine fluor. Cells were washed with wash buffers #1 and #2, and then suspended in a modified mounting solution. The additional compound in the modified mounting solution was varied; as a control, water was used as the additional compound. The signal intensity was observed under the fluorescent microscope. The results are given in Table 6.

The results showed each of the compounds tested was effective as a signal enhancer. The results with dodecyl alcohol were in contrast to an earlier experiment that showed a decrease in signal due to that compound.

TABLE 6

| Additional compound in the Mounting Solution | Signal Intensity Scale of 1 to 4 |
|---|---|
| water | 1 |
| 1,2 propanediol | 4 |
| hydroxypropylcyclodextrin | 2 |
| hexamethyldisiloxane | 2 |
| dodecyl alcohol | 4 |
| pyrrolidinone | 3 |
| isopropyl palmitate | 4 |
| oleyl alcohol | 3 |
| squalane | 3 |
| squalene | 3 |

Having thus described the invention, what is desired to protect by Letters Patent and hereby claim is:

1. A process of detecting a target molecule in a biological entity which process comprises the steps of:
   (1) contacting the biological entity with an assay solution comprising a probe molecule so as to allow the probe molecule to bind to the target molecule, and
   (2) detecting the probe molecule that is in the biological entity after said probe molecule has bound to the target molecule said bound probe detection being indicative of the presence of the target molecule in the biological entity, wherein the assay solution comprises a probe molecule and DMSO (2 to 20 percent) and one or more compounds selected from the group, an alcohol (2 to 20 percent), an aliphatic alkane (2 to 20 percent), an alkene (2 to 20 percent), a fatty acid ester (2 to 20 percent) of the formula $R_1(COO)R_2$, an amide or lactam (2 to 15 percent) of the formula $R_3(NH)(CO)R_4$, and an organic silane (2 to 20 percent) of the formula $(SiR_5R_6R_7)N(SiR_8R_9R_{10})$, $(SiR_5R_6R_7)$—$(SiR_8R_9R_{10})$, $(SiR_5R_6R_7)O(SiR_8R_9R_{10})$, or $(SiR_5R_6O)(SiR_7R_8)(SiR_9R_{10}O)$, the combined volumes of DMSO and the compounds selected from the group not being more than 30 percent of the assay solution (v/v),
   wherein $R_1$, $R_2$, $R_3$, $R_4$, $R_5$, $R_6$, $R_7$, $R_8$, $R_9$, and $R_{10}$ are alkyl moieties, $R_1$ and $R_2$ may be covalently joined to form a ring structure, and $R_3$ and $R_4$ may be covalently joined to form a ring structure, and a percent designated in parenthesis after a compound refers to the compound's concentration expressed as percent of the assay solution (v/v), said probe molecule being a nucleic acid probe,
   said biological entity being either a cell or a virus.

2. A process of claim 1 wherein the alcohol has between 2 and 40 carbon atoms; that aliphatic alkane has between 10 and 60 carbon atoms; the alkene has between 10 and 60 carbon atoms; that $R_1$ plus $R_2$ together have between 3 and 20 carbon atoms and, where $R_1$ and $R_2$ are not covalently joined so as to form a ring, $R_1$ and $R_2$ each have at least 1 carbon atoms; that $R_3$ plus $R_4$ together have between 2 and 20 carbon atoms and, where $R_3$ and $R_4$ are not covalently joined so as to form a ring, $R_3$ and $R_4$ each have at least 1 carbon atom; and that $R_5$, $R_6$, $R_7$, $R_8$, $R_9$ and $R_{10}$, each have at least one carbon atom, that the six alkyl carbon structures, $R_5$, $R_6$, $R_7$, $R_8$, $R_9$ and $R_{10}$, together have no more than 20 carbon atoms.

3. A process of claim 2 wherein the alcohol has between 3 and 30 atoms, aliphatic alkane has between 20 and 40 carbon atoms, the alkene has between 20 and 40 carbon atoms, $R_1$ plus $R_2$ together have between 3 and 10 carbon atoms and, where $R_1$ and $R_2$ are not covalently joined so as to form a ring, $R_1$ and $R_2$ each have at least 3 carbon atoms;

$R_3$ plus $R_4$ together have between 2 and 10 carbon atoms and, where $R_3$ and $R_4$ are not covalently joined so as to form a ring, $R_3$ and $R_4$ each have at least 1 carbon atoms; and and that $R_5$, $R_6$, $R_7$, $R_8$, $R_9$ and $R_{10}$, each have at least one carbon atom, that the six alkyl carbon structures, $R_5$, $R_6$, $R_7$, $R_8$, $R_9$ and $R_{10}$, together have no more than 10 carbon atoms.

4. A process of claim 1 wherein during step (1) the biological entity is suspended in solution and is not immobilized on a solid support.

5. A process of claim 1 wherein during step (1) the biological entity is immobilized on a solid support.

6. A process of claim 1 wherein the biological entity is a cell.

7. A process of claim 6 wherein the cell is a eukaryotic cell.

8. A process of claim 7 wherein the cell is a human cell.

9. A process of claim 8 wherein the probe is specific for viral nucleic acid.

10. A process of claim 6 wherein the cell is a prokaryotic cell.

11. A process of claim 1 where the biological entity is a virus.

12. A process of claim 6 wherein the probe molecule is a nucleic acid molecule.

13. A process of claim 2 wherein the probe molecule is a nucleic acid molecule and the biological entity is a cell.

14. A process of claim 3 wherein the probe molecule is a nucleic acid molecule and the biological entity is a cell.

15. A process of claim 1 wherein the probe molecule is a nucleic acid molecule.

16. A process of claim 9 wherein the viral nucleic acid is human immunodeficiency virus nucleic acid.

17. A process of detecting a target molecule in a biological entity which process comprises the steps of:
   (1) contacting the biological entity with an assay solution comprising a probe molecule so as to allow the probe molecule to bind to the target molecule, and
   (2) detecting the probe molecule after it has bound to the target molecule said bound probe detection being indicative of the presence of the target molecule in the biological entity,
   said assay solution comprising the probe molecule, DMSO, either an aliphatic alkane or an alkene, and at least one other compound selected from the group, an alcohol, a cyclodextrin, a fatty acid ester, an amide or lactam, and an organic silane,
   said probe molecule being either a probe comprising a nucleic acid or a probe comprising an antibody,
   said biological entity being a cell or a virus.

18. A process of claim 17 wherein the assay solution contains about 10 percent of an alcohol derivative of polyoxyethylene ether.

19. The process of claim 17 wherein an alkane and at least one other compound are selected from the group.

20. A process of claim 19 wherein the combined volumes of DMSO and the compounds selected from the group are not more than 20 percent of the assay solution (v/v).

21. A process of claim 20 wherein the concentration of DMSO is about 10 percent.

22. A process of claim 21 wherein the concentration of the alkane is about 5 percent.

23. A process of claim 17 wherein the probe molecule is a nucleic acid molecule and the biological entity is a cell.

24. A process of claim 18 wherein the probe molecule is a nucleic acid molecule and the biological entity is a cell.

25. A process of claim 19 wherein the probe molecule is a nucleic acid molecule and the biological entity is a cell.

26. A process of claim 20 wherein the probe molecule is a nucleic acid molecule and the biological entity is a cell.

27. A process of claim 21 wherein the probe molecule is a nucleic acid molecule and the biological entity is a cell.

28. A process of claim 22 wherein the probe molecule is a nucleic acid molecule and the biological entity is a cell.

29. A process of claim 20 wherein the probe is specific for human immunodeficiency virus nucleic acid.

30. A process of detecting a target molecule in a biological entity which process comprises the steps of:
  (1) contacting the biological entity with an assay solution comprising a probe molecule so as to allow the probe molecule to bind to the target molecule,
  (2) removing the biological entity from the assay solution,
  (3) creating a suspension of the biological entity in a detection solution, said detection solution comprising a signal enhancing compound, and
  (4) while the biological entity is in the suspension created in step (3), detecting a signal that is light quanta generated directly or indirectly by the target-bound probe molecule said bound probe detection being indicative of the presence of the target molecule in the biological entity,
  wherein the detection solution comprises one or more compounds selected from the group, an alcohol (2 to 20 percent), an aliphatic alkane (2 to 20 percent), an alkene (2 to 20 percent), a fatty acid ester (2 to 20 percent) of the formula $R_1(COO)R_2$, an amide or lactam (2 to 15 percent) of the formula $R_3(NH)(CO)R_4$, and an organic silane (2 to 20 percent) of the formula $R_5SiOSiR_6$, wherein $R_1$, $R_2$, $R_3$, $R_4$, $R_5$, and $R_6$, are alkyl carbon structures, the combined volumes of DMSO, if DMSO is present, and the compounds selected from the group not being more than 30 percent of the detection solution (v/v),
  wherein said biological entity is either a cell or virus.

31. A process of claim 30 wherein the light quanta is generated directly by the target-bound probe molecule.

32. A process of claim 30 wherein the probe molecule comprises a fluorescent moiety and the light quanta detected in step (4) is emitted by that moiety.

33. A process of claim 30 wherein the alcohol has between 2 and 40 carbon atoms; that aliphatic alkane has between 10 and 60 carbon atoms; that the alkene has between 10 and 60 carbon atoms, that $R_1$ plus $R_2$ together have between 3 and 20 carbon atoms and, where $R_1$ and $R_2$ are not covalently joined so as to form a ring, $R_1$ and $R_2$ each have at least one carbon atom; that $R_3$ plus $R_4$ together have between 2 and 20 carbon atoms and, where $R_3$ and $R_4$ are not covalently joined so as to form a ting, $R_3$ and $R_4$ each have at least one carbon atom; and that $R_5$ and $R_6$ each have at least one carbon atom, that the alkyl carbon structures, $R_5$ and $R_6$ together have no more than 20 carbon atoms.

34. A process of claim 33 wherein the alcohol has between 3 and 30 carbon atoms; that aliphatic alkane has between 20 and 40 carbon atoms; $R_1$ plus $R_2$ together have between 3 and 10 carbon atoms and, where $R_1$ and $R_2$ are not covalently joined so as to form a ring, $R_1$ and $R_2$ each have at least one carbon atom;
  $R_3$ plus $R_4$ together have between 3 and 10 carbon atoms and, where $R_3$ and $R_4$ are not covalently joined so as to form a ring, $R_3$ and $R_4$ each have at least one carbon atom; and
  $R_5$ and $R_6$ each have at least one carbon atom, that the alkyl carbon structures, $R_5$ and $R_6$ together have no more than 20 carbon atoms.

35. A process of claim 30 wherein the probe molecule is a nucleic acid molecule and the biological entity is a cell.

36. A process of claim 31 wherein the probe molecule is a nucleic acid molecule and the biological entity is a cell.

37. A process of claim 32 wherein the probe molecule is a nucleic acid molecule and the biological entity is a cell.

38. A process of claim 30 wherein the alcohol has between 2 and 40 carbon atoms, the aliphatic alkane has between 10 and 60 carbon atoms; the alkene has between 10 and 60 carbon atoms, that $R_1$ plus $R_2$ together have between 3 and 20 carbon atoms and, where $R_1$ and $R_2$ are not covalently joined so as to form a ring, $R_1$ and $R_2$ each have at least one carbon atom; that $R_3$ plus $R_4$ together have between 2 and 20 carbon atoms and, where $R_3$ and $R_4$ are not covalently joined so as to form a ring, $R_3$ and $R_4$ each have at least one carbon atom; and that $R_5$ and $R_6$ each have at least one carbon atom, that the alkyl carbon structures, $R_5$ and $R_6$ together have no more than 20 carbon atoms.

39. A process of claim 38 wherein the alcohol has between 3 and 30 carbon atoms, the aliphatic alkane has between 20 and 40 carbon atoms, $R_1$ plus $R_2$ together have between 3 and 10 carbon atoms and, where $R_1$ and $R_2$ are not covalently joined so as to form a ring, $R_1$ and $R_2$ each have at least 3 carbon atoms;
  $R_3$ plus $R_4$ together have between 3 and 10 carbon atoms and, where $R_3$ and $R_4$ are not covalently joined so as to form a ring, $R_3$ and $R_4$ each have at least 1 carbon atom; and
  $R_5$ and $R_6$, each have at least one carbon atom, that the alkyl carbon structures, $R_5$ and $R_6$ together have no more than 10 carbon atoms.

40. A process of detecting a target molecule in a biological entity which process comprises the steps of:
  (1) contacting the biological entity with an assay solution comprising a probe molecule so as to allow the probe molecule to bind to the target molecule, and
  (2) detecting the probe molecule that is in the biological entity after said probe molecule has bound to the target molecule said bound probe detection being indicative of the presence of the target molecule in the biological entity,
  wherein the assay solution comprises a cyclodextrin,
  and wherein said biological entity is either a cell or a virus.

41. A process of claim 40 wherein during step (1) the biological entity is suspended in solution and not immobilized on a solid support.

42. A process of claim 40 wherein during step (1) the biological entity is immobilized on a solid support.

43. A process of claim 40 wherein the biological entity is a cell.

44. A process of claim 43 wherein the cell is a eukaryotic cell.

45. A process of claim 44 wherein the cell is a human cell.

46. A process of claim 45 wherein the probe is specific for viral nucleic acid.

47. A process of detecting a target molecule in a biological entity which process comprises the steps of:
   (1) contacting the biological entity with an assay solution comprising a probe molecule so as to allow the probe molecule to bind to the target molecule,
   (2) removing the biological entity from the assay solution,
   (3) creating a suspension of the biological entity in a detection solution, said detection solution comprising a signal enhancing compound, and
   (4) while the biological entity is in the suspension created in step (3), detecting a signal that is light quanta generated directly or indirectly by the target-bound probe molecule said bound probe detection being indicative of the presence of the target molecule in the biological entity,
   said signal enhancing compound selected from the group consisting of an aliphatic alkane, a cyclodextrin, an amide or lactam, and an organic silane,
   wherein said biological entity is either a cell or virus.

48. A process of claim 47 wherein the signal enhancing compound is a cyclodextrin.

49. A process of claim 47 wherein the signal enhancing compound is an aliphatic alkane.

50. A process of claim 47 wherein the signal enhancing compound is an amide or lactam.

51. A process of claim 47 wherein the signal enhancing compound is an organic silane.

52. A kit that comprises a probe molecule and an assay solution that comprises DMSO and squalane and one or more compounds selected from the group, an alcohol, a fatty acid ester, an amide or lactam, and an organic silane, the combined volumes of DMSO and squalane and the compound or compounds selected from the group not being more than about 20 percent of the solution (v/v), the volume of DMSO being between about 2 percent and 16 percent of the solution (v/v), the amount of squalane being between about 2 percent and 16 percent of the solution (v/v).

53. A kit that comprises a probe molecule and a solution that comprises DMSO (2 to 20 percent) and one or more compounds selected from the group, an alcohol (2 to 20 percent), an aliphatic alkane (2 to 20 percent), an alkene (2 to 20 percent), a fatty acid ester (2 to 20 percent) of the formula $R_1(COO)R_2$, an amide or lactam (2 to 15 percent) of the formula $R_3(NH)(CO)R_4$, and an organic silane (2 to 20 percent) of the formula $(SiR_5R_6R_7)N(SiR_8R_9R_{10})$, $(SiR_5R_6R_7)—(SiR_8R_9R_{10})$, $(SiR_5R_6R_7)O(SiR_8R_9R_{10})$, or $(SiR_5R_6O)(SiR_7\ R_8O)(SiR_9R_{10}O)$, the combined volumes of DMSO and the compounds selected from the group not being more than 30 percent of the solution (v/v),
   wherein $R_1$, $R_2$, $R_3$, $R_4$, $R_5$, $P_6$, $R_7$, $R_8$, $P_9$, and $R_{10}$ are alkyl moieties, $R_1$ and $R_2$ may be covalently joined to form a ring structure, and $R_3$ and $R_4$ may be covalently joined to form a ring structure, and a percent designated in parenthesis after a compound refers to the compound's concentration expressed as percent of the solution (v/v),
   said probe molecule being a nucleic acid probe.

54. A solution comprising a probe molecule and DMSO (2 to 20 percent) and one or more compounds selected from the group, an alcohol (2 to 20 percent), an aliphatic alkane (2 to 20 percent), an alkene (2 to 20 percent), a fatty acid ester (2 to 20 percent) of the formula $R_1(COO)R_2$, an amide or lactam (2 to 15 percent) of the formula $R_3(NH)(CO)R_4$, and an organic silane (2 to 20 percent) of the formula $(SiR_5R_6R_7)N(SiR_8R_9R_{10})$, $(SiR_5R_6R_7)—(SiR_8R_9R_{10})$, $(SiR_5R_6R_7)O(SiR_8R_9R_{10})$, or $(SiR_5R_6O)(SiR_7R_8O)(SiR_9R_1O)$, the combined volumes of DMSO and the compounds selected from the group not being more than 30 percent of the assay solution (v/v),
   wherein $R_1$, $R_2$, $R_3$, $R_4$, $R_5$, $R_6$, $R_7$, $R_8$, $R_9$, and $R_{10}$ are alkyl moieties, $R_1$ and $R_2$ may be covalently joined to form a ring structure, and $R_3$ and $R_4$ may be covalently joined to form a ring structure, and a percent designated in parenthesis after a compound refers to the compound's concentration expressed as percent of the solution (v/v), wherein said probe molecule is a nucleic acid probe.

55. A solution that comprises a probe and DMSO and squalane and one or more compounds selected from the group, an alcohol, a fatty acid ester, an amide or lactam, and an organic silane, the combined volumes of DMSO and squalane and the compound or compounds selected from the group not being more than about 20 percent of the solution (v/v), the volume of DMSO being between about 2 per cent and 16 percent of the solution (v/v), the amount of squalane being between about 2 percent and 16 percent of the solution (v/v), said probe being a nucleic acid molecule.

56. A solution of claim 28 wherein the alcohol has between 2 and 40 carbon atoms; that aliphatic alkane has between 10 and 60 carbon atoms; the alkene has between 10 and 60 carbon atoms; that $R_1$ plus $R_2$ together have between 3 and 20 carbon atoms and, where $R_1$ and $R_2$ are not covalently joined so as to form a ring, $R_1$ and $R_2$ each have at least 1 carbon atoms; that $R_3$ plus $R_4$ together have between 2 and 20 carbon atoms and, where $R_3$ and $R_4$ are not covalently joined so as to form a ring, $R_3$ and $R_4$ each have at least 1 carbon atom; and that $R_5$, $R_6$, $R_7$, $R_8$, $R_9$ and $R_{10}$, each have at least one carbon atom, that the six alkyl carbon structures, $R_5$, $R_6$, $R_7$, $R_8$, $R_9$ and $R_{10}$, together have no more than 20 carbon atoms.

57. A solution of claim 56 wherein the alcohol has between 3 and 30 atoms, aliphatic alkane has between 20 and 40 carbon atoms, the alkene has between 20 and 40 carbon atoms, $R_1$ plus $R_2$ together have between 3 and 10 carbon atoms and, where $R_1$ and $R_2$ are not covalently joined so as to form a ring, $R_1$ and $R_2$ each have at least 3 carbon atoms;

$R_3$ plus $R_4$ together have between 2 and 10 carbon atoms and, where $R_3$ and $R_4$ are not covalently joined so as to form a ring, $R_3$ and $R_4$ each have at least 1 carbon atoms;

and that $R_5$, $R_6$, $R_7$, $R_8$, $R_9$ and $R_{10}$, each have at least one carbon atom, that the six alkyl carbon structures, $R_5$, $R_6$, $R_7$, $R_8$, $R_9$ and $R_{10}$, together have no more than 10 carbon atoms.

* * * * *